United States Patent
Yim et al.

(12)

(10) Patent No.: US 9,851,333 B2
(45) Date of Patent: Dec. 26, 2017

(54) NEBULIZER FOR CHARGED AEROSOL DETECTION (CAD) SYSTEM

(71) Applicant: DIONEX CORPORATION, Sunnyvale, CA (US)

(72) Inventors: Alan Daniel Yim, Plainville, MA (US); Paul H. Gamache, Hudson, NH (US); Ryan S. McCarthy, Lowell, MA (US)

(73) Assignee: Dionex Corporation, Sunnyvale, CA (US)

( * ) Notice: Subject to any disclaimer, the term of this patent is extended or adjusted under 35 U.S.C. 154(b) by 575 days.

(21) Appl. No.: 14/288,693

(22) Filed: May 28, 2014

(65) Prior Publication Data

US 2014/0352411 A1    Dec. 4, 2014

Related U.S. Application Data

(60) Provisional application No. 61/828,629, filed on May 29, 2013.

(51) Int. Cl.
*G01N 30/96* (2006.01)
*G01N 30/84* (2006.01)
(Continued)

(52) U.S. Cl.
CPC ............ *G01N 30/84* (2013.01); *G01N 30/64* (2013.01); *B05B 7/0012* (2013.01);
(Continued)

(58) Field of Classification Search
CPC .............................................. G01N 2030/8452
See application file for complete search history.

(56) References Cited

U.S. PATENT DOCUMENTS 2,720,308 A * 10/1955 Howell, Jr. ............ B65D 55/02
                                                              206/325
5,098,657 A    3/1992 Blackford et al.
(Continued)

OTHER PUBLICATIONS

Dixon, "Development and Testing of a Detection Method for Liquid Chromatography Based on Aerosol Charging," Anal. Chem., 74, 2930-2937, 2002.
(Continued)

*Primary Examiner* — Laura Martin
*Assistant Examiner* — Alex Devito
(74) *Attorney, Agent, or Firm* — Thomas F. Cooney; Charles B. Katz

(57) ABSTRACT

A nebulizer for a charged aerosol detection (CAD) system is disclosed. The nebulizer is provided with a spray emitter for generating a spray of droplets within a central region of a spray chamber. The central region is separated from an upper region by a horizontally projecting rib, which defines a passageway between the central and upper regions. The major direction of droplet travel within the upper region is substantially reversed with respect to the major direction of droplet travel within the central region. Larger droplets are unable to negotiate the turn from the central to upper regions and impinge on a rear surface of the spray chamber. Removal of larger droplets has the advantageous effect of enabling the detector to sense a smaller range of particle sizes, which establishes a relatively steady electrical current at the detector.

9 Claims, 4 Drawing Sheets

Figure 3:
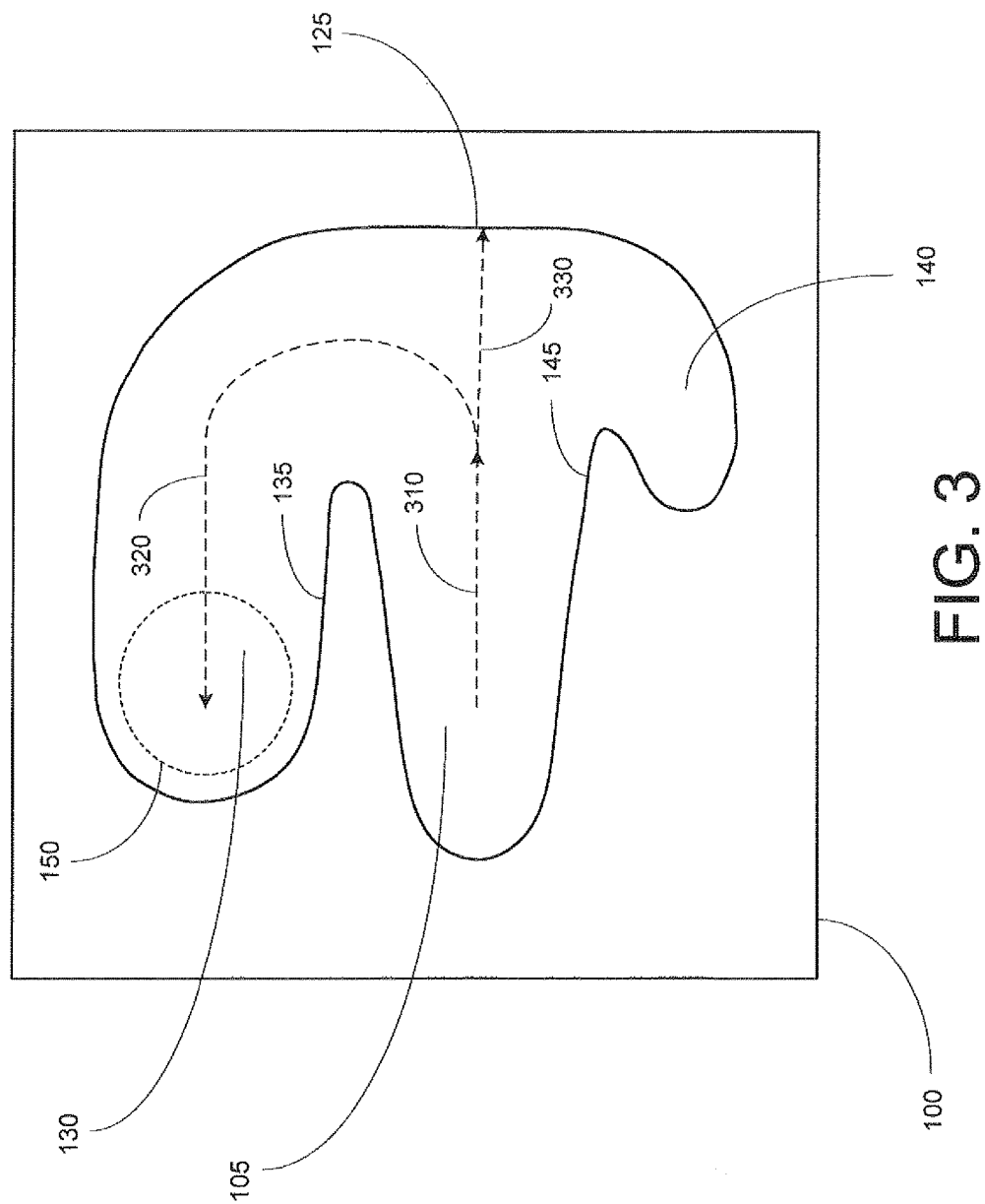

(51) Int. Cl.
  *G01N 30/64* (2006.01)
  *B05B 7/00* (2006.01)
  *B05B 7/08* (2006.01)
(52) U.S. Cl.
  CPC ...... *B05B 7/0876* (2013.01); *G01N 2030/847* (2013.01); *G01N 2030/8452* (2013.01); *G01N 2030/8464* (2013.01)

(56) References Cited

U.S. PATENT DOCUMENTS

| | | |
|---|---|---|
| 5,247,842 A | 9/1993 | Kaufman et al. |
| 6,568,245 B2 | 5/2003 | Kaufman |
| 2007/0023677 A1* | 2/2007 | Perkins ................. H01J 49/107 250/425 |
| 2012/0105839 A1* | 5/2012 | Novosselov ......... G01N 1/2208 356/301 |

OTHER PUBLICATIONS

Merriam-Webster, "Definition of Aerosol", http://www.merriam-webster.com/dictionary/aerosol, retrieved Nov. 2, 2016, pp. 1-3.
Vehovec, et al., "Review of operating principle and applications of the charged aerosol detector", Journal of Cinematography A, 1217 (2010) pp. 1549-1556.
Wikipedia, "Aerosol", https://en.wikipedia.org/wiki/Aerosol, retrieved Nov. 1, 2016, pp. 1-14.

* cited by examiner

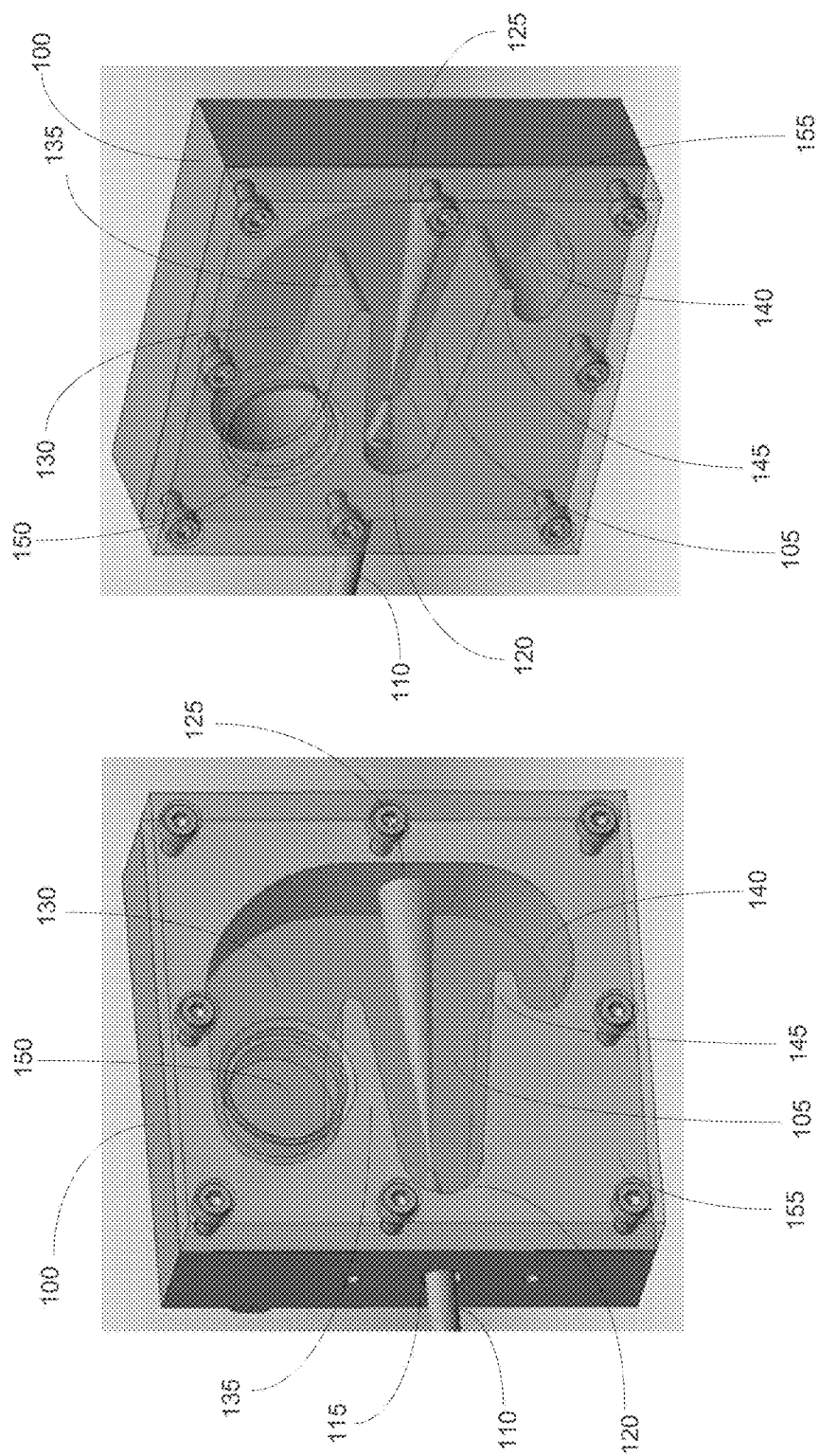

NEBULIZER FOR CHARGED AEROSOL DETECTION (CAD) SYSTEM

CROSS-REFERENCE TO RELATED APPLICATIONS

This application claims the priority benefit of U.S. Provisional Patent Application No. 61/828,629 for "Nebulizer for Charged Aerosol Detection (CAD) System", filed May 29, 2013, the disclosure of which is hereby incorporated by reference.

FIELD OF THE INVENTION

The present invention relates generally to devices for detecting and quantifying components of a liquid sample stream, and more particularly to a nebulizer for use with a charged aerosol detection system.

BACKGROUND OF THE INVENTION

Charged aerosol detection is a popular and valuable technique for the detection and quantification of substances present in a liquid sample stream, and is particularly well-suited to use in connection with liquid chromatography applications. Briefly described, a charged aerosol detection (CAD) system consists of a nebulizer for generating a spray of droplets from a liquid sample stream (for example, the effluent from a chromatographic column), a discharge source for selectively charging the nonvolatile residue particles produced by drying the droplet spray, and a collector, where the aggregate charge imparted to the particles is measured using an electrometer. The resultant signal is representative of the concentration of the nonvolatile components of the sample stream. CAD is sometimes referred to as a "universal" detection technique, as it is capable of quantifying a wide variety of nonvolatile substances with consistent response. Further details regarding the design, operation and advantages of CAD systems are set forth in U.S. Pat. No. 6,568,245 by Kaufman ("Evaporative Electrical Detector"), the disclosure of which is incorporated herein by reference.

The performance of a CAD system is closely tied to the parameters of the droplet spray produced within the nebulizer. It is generally desirable to generate a spray of droplets of uniformly small diameters, since droplets having relatively large diameters may not have adequate time to dry (i.e., to fully evaporate the solvent) and form particles of non-volatile residue prior to reaching the discharge source, which may in turn compromise the ability of the CAD system to quantify analytes contained within the droplets with high degrees of sensitivity and reproducibility. Prior art CAD systems, such as the one described in the aforementioned Kaufman patent, have commonly utilized a nebulizer in which the liquid sample stream is introduced transversely to a jet of compressed air, which is directed at a velocity sufficient to break the sample stream into droplets. Spray generation is assisted by the action of an impactor, which is located proximate to the intersection of the liquid and gas flows. The smaller droplets travel within the nebulizer under the influence of the entraining gas to the nebulizer exit, and pass thereafter to the discharge source. Larger droplets, having greater momentum, impinge on the surface of the impactor and are either broken into smaller droplets or removed to waste through a drain positioned below the impactor.

While prior art CAD system nebulizers have produced generally acceptable results, there remains a need in the art for improved nebulizer designs in order to facilitate more sensitive and reliable detection.

SUMMARY

In accordance with certain illustrative embodiments of the invention, a nebulizer for a CAD system is provided having an emitter for generating a droplet spray, and a spray chamber having a central region into which the droplet spray is introduced. The spray chamber further includes a rear surface positioned opposite to the emitter outlet, and a partition dividing the central region from an upper region and defining a passageway through which a portion of the droplets in the droplet spray travel. The central and upper regions are arranged such that the major direction of droplet travel within the upper region is substantially reversed with respect to the major direction of ion travel in the central region. Larger droplets in the droplet spray are unable to negotiate the "hairpin turn" required to pass from the central region to the upper region and impact the rear surface of the spray chamber. The separation of the large droplets from the droplet spray via this mechanism has the advantageous effect of enabling the detector of the CAD system to sense a smaller range of particle sizes, which establishes a relatively steady electrical current at the detector. This steady baseline electrical current facilitates the identification of higher electrical currents or peaks as samples are injected and separated in the chromatographic column and subsequently introduced to the nebulizer.

In accordance with another embodiment of the invention, a method is provided for detecting analytes in a liquid sample stream. The method includes steps of introducing the liquid sample stream as a droplet spray into a spray chamber, and causing the major direction of droplet travel to be reversed within the spray chamber, such that a portion of the droplets (e.g., larger droplets) impact a spray chamber surface and are removed from the droplet spray. The remaining droplets are then conveyed to an exit of the spray chamber, and the volatile solvent fraction is evaporated (e.g., by passing the droplets through a heated evaporator tube) to produce particles of non-volatile analyte material. The particles of analyte material are then charged in a charging chamber (for example, by interacting with an ionized gas stream), and the aggregate charge imparted to the particles is subsequently measured by a collector device comprising an electrometer.

BRIEF DESCRIPTION OF THE FIGURES

In the accompanying drawings:

FIGS. 1 and 2 are perspective views of a CAD system nebulizer constructed in accordance with an illustrative embodiment of the invention;

FIG. 3 is an elevational view depicting the interior of the spray chamber body;

FIG. 4 is a partial cross-sectional view of a spray emitter; and

FIG. 5 is a symbolic diagram of a CAD system implementing a nebulizer constructed according to the invention.

DETAILED DESCRIPTION OF EMBODIMENTS

FIGS. 1-3 depict a nebulizer constructed in accordance with an embodiment of the present invention. The nebulizer includes a spray chamber body 100 having a central region 105 into which the sample spray is introduced by means of a pneumatic spray emitter 110, which is positioned within a port 115 penetrating the front wall 120. The tip of emitter 110 is horizontally spaced from (note: the terms "horizontal", "vertical" and their variants are used herein for ease of explanation, and should not be construed as limiting the spray chamber to any particular orientation) and positioned in opposition to a medial portion (alternatively referred to herein as the "rear surface") of back wall 125. Spray chamber further includes an upper region 130 partially divided from central region 105 by means of a horizontally projecting rib or partition 135, and a lower region 140 partially divided from central region 105 by means of a horizontally projecting rib or partition 145.

Figure 4:
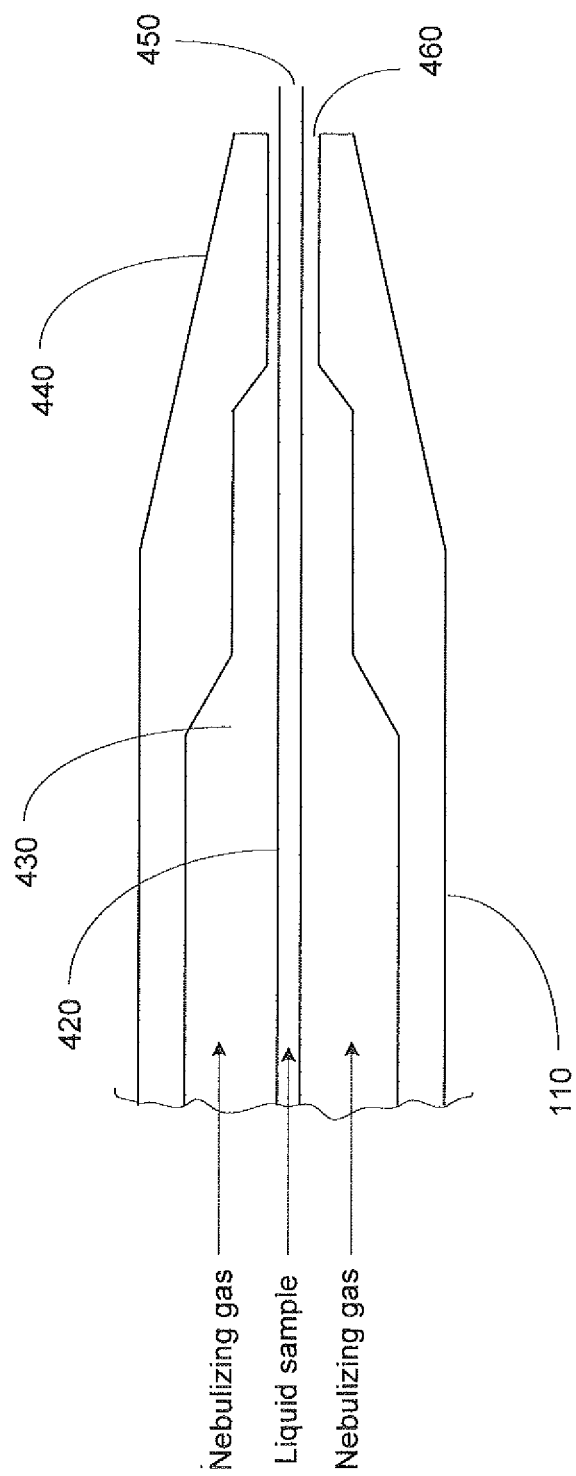

Referring now to FIG. 4, spray emitter 110 may take the form of a pneumatic emitter of the type used in atmospheric pressure chemical ionization (APCI) sources for mass spectrometers. Spray emitter 110 is provided with a central passageway through which the liquid sample flows from an inlet end to an exit end of emitter 110. The central passageway may be defined interiorly of a capillary 420 extending longitudinally through the spray emitter body. As discussed above, the liquid sample may be the effluent of a chromatographic column, which operates to separate compounds or groups of compounds within the sample such that different compounds are introduced into the nebulizer at different times. Spray emitter 110 is further provided with one or more gas passageways 430, arranged around the central passageway, through which a nebulizing gas flow is directed. The gas will typically be supplied from a source of compressed gas, e.g., a bottle of compressed air or nitrogen. Emitter 110 terminates in a nozzle 440, at which the liquid and gas flows pass into the interior of spray chamber 100 to form a droplet spray. In certain implementations of spray emitter 110, the liquid and gas flows may exit the emitter nozzle through separate orifices (depicted as 450 and 460, respectively) and interact thereafter within the spray chamber 100 to form the spray cone; the gas passageway orifice(s) may consist, for example, of a continuous annular orifice circumscribing the liquid sample orifice (as shown in FIG. 4), or a plurality of discrete orifices disposed radially around the liquid sample orifice. The gas passageway and liquid orifices are sized to optimize spray and other operational characteristics: the liquid orifice should be sufficiently small to produce droplets of relatively small diameters, but excessively small orifice sizes that are prone to frequent clogging and/or require unacceptably high pressures at the emitter inlet should be avoided; the gas orifice(s) should be sized to establish shear forces at and near the nozzle tip sufficient to produce a high-quality, stable spray of uniformly small droplets. In other implementations, the liquid and gas flows may be mixed within a chamber interior to the nozzle and exit the nozzle tip via a common orifice. In contradistinction to the nebulizer design shown in the Kaufman patent, the liquid and gas flows at the nozzle are co-directional; otherwise expressed, the central axes of the principal initial direction of motion of the liquid and gas flows (i.e., in the horizontal direction) are co-axial or parallel.

As depicted in FIG. 3, droplets formed at the emitter nozzle travel principally in the horizontal direction (referred to as the major direction) toward back wall 125, as indicated by dotted line 310. The volatile portion of the droplets (e.g., solvent) is evaporated from the droplet surface as they traverse the central region, resulting in a reduction in their size and mass. Droplets of sufficiently small size/mass are entrained by the gas flow and negotiate a "hairpin" turn (in which the major direction of droplet travel is substantially reversed within relatively short distance) to pass into upper region 130. The gas flow and entrained droplets (as well as particles of non-volatile analytes formed from fully dried droplets) travel through the upper region from right to left in a major direction substantially reversed with respect to the major direction of droplet travel within central region 105 (as indicated by dotted line 320), and pass thereafter into exit port 150. Evaporation of any residual volatile component continues as the droplets travel through upper region 130. Exit port 150 communicates with a charging chamber where, as described above, the nonvolatile residue particles are electrically charged for subsequent detection.

It is noted that the portion of back wall 125 extending upwardly of the medial portion of central region 105 and into upper region 130 is curved, with a relatively large radius of curvature. This geometry assists in maintaining a smooth flow of gas (and the entrained droplets) into upper region 130, and avoids the creation of eddies or other turbulent flow patterns that may adversely affect stability or produce excessive deposition of the droplets or dried particles on the spray chamber walls. The portion of back wall 125 extending downwardly from the medial portion into lower region 140 is preferably gently curved as well, in order to promote the transport of accumulated liquid (resulting from the impact of the larger droplets) to the drain.

Relatively large droplets formed in the droplet spray are unable to negotiate the turn into upper region 130 due to their higher momentum, and instead impact the medial portion of back wall 125, as indicated by dotted line 330. The resultant liquid accumulated on back wall 125 flows into lower region 140 under the influence of gravity, and may be continuously or periodically removed therefrom via a drain port. The separation of the large droplets from the droplet spray via this mechanism has the advantageous effect of enabling the detector to sense a smaller range of particle sizes, which establishes a relatively steady electrical current at the detector. This steady baseline electrical current facilitates the identification of higher electrical currents or peaks as samples are injected and separated in the chromatographic column and subsequently introduced to the nebulizer.

As is known in the art, the characteristics of the spray (e.g., droplet size distribution and spray cone angle) produced by emitter 110 will vary according to a number of operational and design parameters, including the viscosity and surface tension of the liquid sample, the geometry and dimensions of the liquid and gas orifices, and the liquid and gas flow rates. For the emitter design depicted in FIG. 4, which has a nozzle orifice diameter of approximately 450 µm, good performance has been achieved for a variety of applications when spray emitter 110 is operated with a gas flow rate of between 2.0 and 3.5 liters/minute and a liquid flow rate of between 0.1 and 2.5 ml/minute. The gas flow rate will typically be controlled and adjusted by means of a valve or other metering device. The liquid flow rate will typically be controlled, at least in part, by adjustment of the liquid chromatography (LC) pump or other apparatus that delivers the liquid sample to the spray emitter inlet.

In certain implementations, it may be desirable to control the temperature (heat or cool) spray emitter 110 and/or spray chamber 100 in order to optimize spray characteristics, or to promote solvent evaporation. Any suitable temperature control device, such as a cartridge heater, may be used for this purpose.

It has been observed that the performance of the nebulizer and associated CAD system is influenced by the placement of the emitter nozzle tip relative to the opposing portion of back wall 125. Generally good results have been achieved, using the emitter design of FIG. 4 and the operating parameters outlined above, when the distance between the emitter nozzle tip and back wall 125 is about 50 mm. This distance may be fixed; in alternative embodiments, spray emitter 110 may be slidably positionable within port 115, such that the distance to the back wall may be adjusted by the user to optimize results.

The interior of spray chamber body 100 may be sealed to the outside by means of a plate cover 155 (depicted transparently in FIGS. 1 and 2 to reveal the spray chamber interior) and a gasket interposed between facing surfaces of the spray chamber body and cover. The cover may be secured to spray chamber body 100 using screws or other removable fasteners. The cover and spray chamber body may be fabricated from any suitable material, such as stainless steel, that is substantially non-reactive with respect to the substances to be analyzed. Surfaces of the cover and spray chamber body forming the spray chamber interior should have finishes that are sufficiently smooth to prevent the development of turbulence. When assembled, the nebulizer unit will typically have a relatively thin aspect, with its depth being significantly smaller relative to its horizontal (width) and vertical (height) dimensions.

Figure 5:
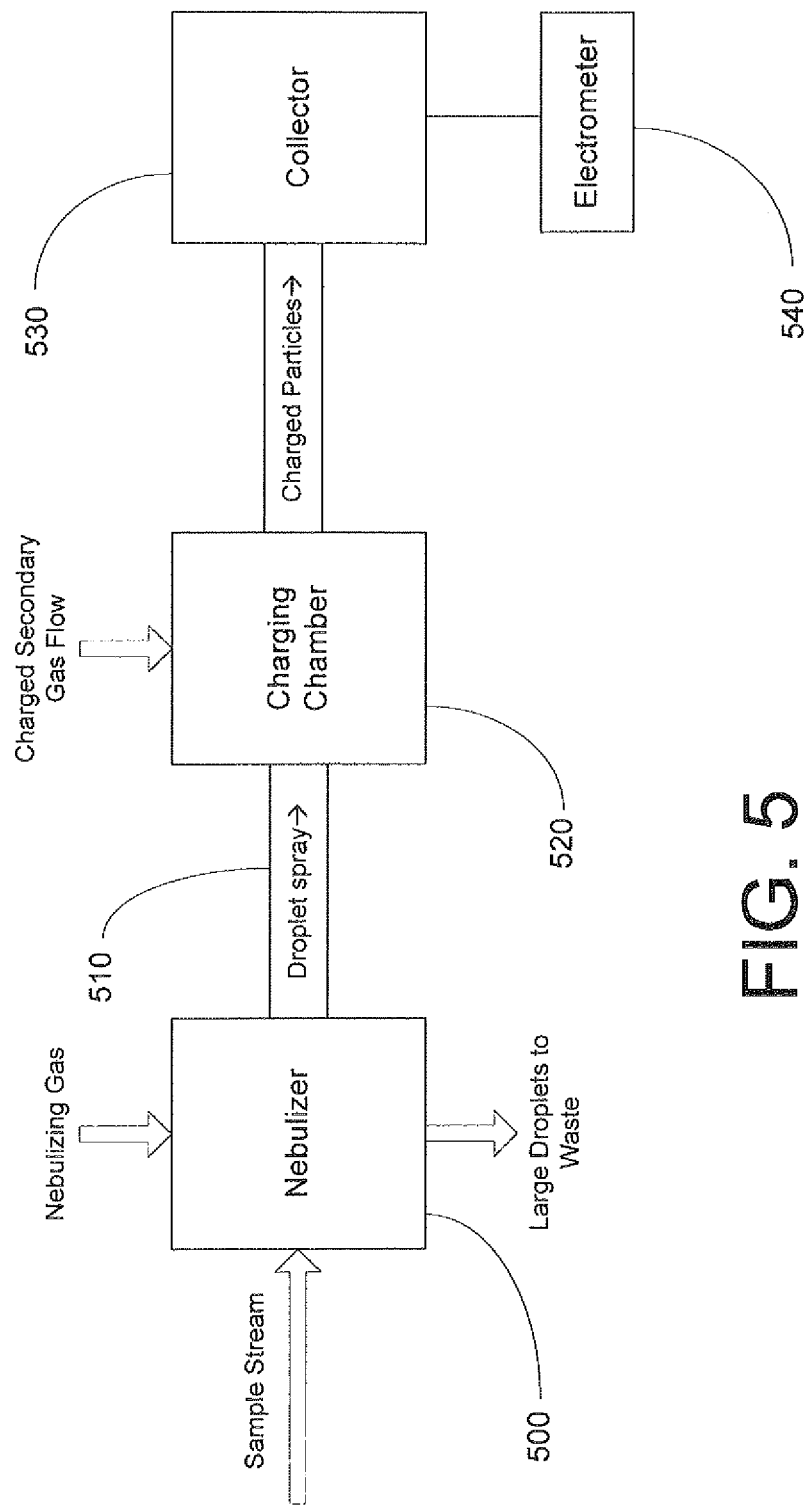

FIG. 5 depicts a CAD system incorporating a nebulizer constructed in accordance an embodiment of the invention. Nebulizer 500, which may take the form of the nebulizer depicted in FIGS. 1-3 and described above, receives a liquid sample stream from, for example, the effluent from the liquid chromatography column. In addition to the liquid sample stream, a nebulizer gas flow is directed into nebulizer 500 for the purpose of generating the droplet spray, as described above. A portion of the droplets in the droplet spray (those of sufficiently small size to negotiate the reversed-direction trajectory defined within the spray chamber), entrained in the gas stream, are conveyed through a evaporator tube 510 into a charging chamber 520. Larger droplets impact surfaces within the spray chamber, and are thereby removed from the droplet spray. Within evaporator tube 510, volatile solvent is evaporated from the droplets to form particles of non-volatile analyte material. Charge from an ionized gas stream is transferred to the analyte particles in charging chamber 520, with the amount of charge transferred being related to the particle size. The charged particles are then sent to a collector 530, where the aggregate charge imparted to the particles is measured using an electrometer 540, which generates a signal representative of the analyte abundance. This signal is then processed and stored to generate a chromatogram depicting the variation in the intensity of detected analyte as a function of chromatographic retention time.

It should be recognized that while embodiments of the invention are described herein with reference to a conventional pneumatically-driven spray emitter, the principles of the invention (more particularly, the use of a spray chamber having a configuration and geometry that promotes effective spray generation, drying, and separation of large droplets) may be advantageously employed in connection with other types of spray emitters, such as those driven by electrostatic repulsion or the application of pulsation by a piezoelectric element.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A charged aerosol detection (CAD) nebulizer, comprising:

an emitter for generating a droplet spray;

a spray chamber having a central region into which the droplet spray is introduced and a rear surface positioned opposite an outlet of the emitter, the spray chamber including a partition dividing the central region from an upper region and defining a passageway between the central and upper regions through which a portion of the droplets in the droplet spray travel, the upper region communicating with an exit of the spray chamber through which the portion of the droplets in the droplet spray travel, the exit communicating with an aerosol particle detector;

a major direction of droplet travel within the upper region being substantially reversed with respect to the major direction of droplet travel within the central region;

whereby larger droplets within the droplet spray are unable to negotiate the passageway from the central to the upper region and impact the rear surface.

2. The nebulizer of claim 1, wherein the emitter includes a central conduit through which a flow of liquid is directed, and at least one gas conduit through which a nebulizing gas flow is directed.

3. The nebulizer of claim 2, wherein the liquid and nebulizing gas flows mix within a nozzle of the nebulizer and exit a tip of the nozzle through a common orifice.

4. The nebulizer of claim 2, wherein the liquid and nebulizing gas flows exit a tip of the nozzle through separate orifices.

5. The nebulizer of claim 4, wherein the liquid and nebulizing gas flow axes are substantially co-directional.

6. The nebulizer of claim 1, wherein a central axis defined by droplet travel within the central region is substantially parallel to a central axis defined by droplet travel within the upper region.

7. The nebulizer of claim 1, wherein the spray chamber further includes a lower region and a partition dividing the central region from the lower region.

8. The nebulizer of claim 1, wherein the outlet of the emitter is positioned approximately 50 mm from the rear surface.

9. The nebulizer of claim 1, wherein the distance between the tip of the emitter and the rear surface is adjustable.

* * * * *